(12) United States Patent
Martin et al.

(10) Patent No.: US 6,562,577 B2
(45) Date of Patent: *May 13, 2003

(54) PROCEDURE FOR THE ANALYSIS OF BIOLOGICAL SUBSTANCES IN A CONDUCTIVE LIQUID MEDIUM

(75) Inventors: Jean-Rene Martin, Lozanne (FR); Eliane Souteyrand, Ecully (FR); Marcus Francois Lawrence, Chambly (CA); Susan Rosalie Mikkelsen, Montreal (CA)

(73) Assignees: L'Ecole Centrale de Lyon, Ecully (FR); Le Centre National de la Recherche Scientifique, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 10/046,237

(22) Filed: Jan. 16, 2002

(65) Prior Publication Data

US 2002/0061536 A1 May 23, 2002

Related U.S. Application Data

(63) Continuation of application No. 09/660,189, filed on Sep. 12, 2000, now Pat. No. 6,355,436, which is a continuation of application No. 09/137,964, filed on Aug. 21, 1998, now Pat. No. 6,150,106, and a division of application No. 08/649,985, filed on May 17, 1996, now Pat. No. 5,869,244.

(51) Int. Cl.[7] ............................................. C12Q 1/68
(52) U.S. Cl. ............................................. 435/6; 435/6
(58) Field of Search ...................... 435/6, 7.1, 91.1, 435/91.2, 285.2, 287.2; 536/22.1, 23.1, 24.3–24.33

(56) References Cited

U.S. PATENT DOCUMENTS

| | | |
|---|---|---|
| 4,072,576 A | 2/1978 | Arwin et al. |
| 4,238,757 A | 12/1980 | Schenck |
| 4,314,821 A | 2/1982 | Rice |
| 4,444,892 A | 4/1984 | Malmros |
| 4,900,423 A | 2/1990 | Iida et al. |
| 5,160,597 A | 11/1992 | Colapicchioni et al. |
| 5,312,527 A | 5/1994 | Mikkelsen et al. |
| 5,527,670 A | 6/1996 | Stanley |
| 5,556,752 A | 9/1996 | Lockhart et al. |
| 5,565,322 A | 10/1996 | Heller |
| 5,605,662 A | 2/1997 | Heller et al. |
| 5,632,957 A | 5/1997 | Heller et al. |
| 5,653,939 A | 8/1997 | Hollis et al. |
| 5,824,477 A | 10/1998 | Stanley |
| 5,849,486 A | 12/1998 | Heller et al. |
| 5,849,489 A | 12/1998 | Heller |
| 5,869,244 A * | 2/1999 | Martin et al. ............... 435/6 |
| 5,965,452 A | 10/1999 | Kovacs |
| 6,013,166 A | 1/2000 | Heller |
| 6,017,696 A | 1/2000 | Heller |
| 6,033,850 A | 3/2000 | Purvis |
| 6,051,380 A | 4/2000 | Sosnowski et al. |
| 6,071,394 A | 6/2000 | Cheng et al. |
| 6,129,828 A | 10/2000 | Sheldon, III et al. |
| 6,150,106 A * | 11/2000 | Martin et al. ............... 435/6 |
| 6,162,603 A | 12/2000 | Heller |
| 6,355,436 B1 * | 3/2002 | Martin et al. ............... 435/6 |

FOREIGN PATENT DOCUMENTS

| | | |
|---|---|---|
| JP | 62163960 | 7/1987 |
| JP | 244326 | 11/1987 |
| JP | 4186152 | 7/1992 |
| WO | WO 90/05300 | 5/1990 |
| WO | WO 93/22678 | 11/1993 |
| WO | WO 97/08293 | 3/1997 |
| WO | WO 97/41219 | 11/1997 |
| WO | WO 97/43445 | 11/1997 |

OTHER PUBLICATIONS

Briggs, Journal of Parenteral Science & Technology 45(1):7–12 (Jan.–Feb. 1991).
Millan et al, Anal. Chem., 65:2317–2323 (1993).
Lal, Bioelectrochemisty & Bioenergetics, 27:111–139 (1992).

* cited by examiner

*Primary Examiner*—Jeffrey Siew
(74) *Attorney, Agent, or Firm*—Morgan, Lewis & Bockius LLP

(57) ABSTRACT

The present invention relates to a procedure for the qualitative and/or quantitative analysis of biological substances, which are preferably biological substances, that are present in a conductive liquid medium, with the aid of at least one affinity sensor that includes at least one structure that includes at least one semiconductor material, which is coated on one of its surface with at least one layer of an isolating material, which in turn is affixed adhesively to at least one sensitive membrane, which is in contact with the conductive medium and which includes ligands that are complementary to the biological substances in question and which are capable of, and suitable for, forming pairs specifically with the latter biological substances, with the said procedure being characterized by the fact that it consists essentially of applying a voltage between the semiconductor and the conductive medium; of gathering the variations in the electrical signals induced by a charge-effect phenomenon directly and essentially linked to the specific pairings of the biological substances with their complementary ligands included in the sensitive membrane; and interpreting the collected signals in order to identify and/or quantify the substances in question.

12 Claims, 8 Drawing Sheets

PROCEDURE FOR THE ANALYSIS OF BIOLOGICAL SUBSTANCES IN A CONDUCTIVE LIQUID MEDIUM

CROSS REFERENCE TO RELATED APPLICATIONS

This is a continuation of application Ser. No. 09/660,189, filed Sep. 12, 2000, now U.S. Pat. No. 6,355,436; which is a continuation of application Ser. No. 09/137,964, filed Aug. 21, 1998, now U.S. Pat. No. 6,150,106; which is a division of application Ser. No. 08/649,985, filed May 17, 1996, now U.S. Pat. No. 5,869,244.

BACKGROUND OF THE INVENTION

I. Field of the Invention

The present invention generally relates to the detection of products, and preferably of biological products (known as "affins"), especially those with a high molecular weight, such as nucleic acids and biopolymers of a proteic nature, e.g. proteins, peptides and the like. More specifically, in one aspect, the present invention relates to a procedure for the qualitative and/or quantitative analysis of substances (and preferably of biological substances) that are present in a conductive liquid medium ("LC"), by means of electrical measurements. In a related aspect, the present invention provides bioelectronic or biochemical affinity sensors intended for use in the implementation of the detection methods of the invention.

In particularly preferred aspects, the methods and apparatuses of the invention are used in the detection of nucleic acids, e.g., RNA and DNA, and all genetic structures that contain them, as well as compounds that are capable of being involved in immunological coupling reactions, e.g., antigens (Ag) and antibodies (Abs).

II. Background

In order to detect, identify, or quantify nucleic acids, antibodies, antigens and the like, use has been made of their bioaffinity properties, i.e., their ability to specifically pair with their complements, in accordance with genetic hybridization or immunological coupling mechanisms.

For example, typical immunological methods are based on the antigen/antibody coupling mechanism, and involve detection of the resulting antigen/antibody pairs with the aid of radioactive, fluorescent, stained, or similar enzymatic markers. Such methods have proven to be time-consuming and complex to implement. Furthermore, the reactions that are utilized are tedious and not readily available. Finally, these methods do not allow measurements to be made continuously, much less in vivo. Similar methods with similar drawbacks have also been used in the detection of nucleic sequences.

In another approach, detection methods have been proposed that rely on the detection of a number of different physical signals that can be induced by the biochemical nucleotide hybridization or immunological coupling reactions. To do so, it is first generally necessary to isolate a particular and characteristic type of signal and then to utilize a transducer that is suitable for converting that signal into a measurable physical magnitude. For example, the signal may consist of the production of a chemical species, a change in thickness, a change in the optical index, a change in mass, or even a change in electrical charge. Consequently, the transducers may consist of electrochemical, piezoelectric, optical, or electrical sensors. Despite these proposed methods, difficulties still exist in the detection of specific signals indicating that pairing has taken place, and in the development of a corresponding transducer that is reliable, sensitive, and dependable.

SUMMARY OF THE INVENTION

The present invention generally provides methods and apparatuses for the detection of biological substances in conductive liquid media. In a first aspect, the methods of the present invention comprise providing at least one affinity sensor which includes at least one structure having at least one semiconductor (Sc) material coated on one surface with at least one isolating layer (Is) and at least one sensitive membrane (Mbs) affixed to said isolating layer. The sensitive membrane is in fluid contact with a conductive medium (LC) and includes ligands that are complementary to and capable of forming hybridizing pairs with the biological substances to be detected. A voltage is applied between the semiconductor and the conductive medium and variations in electrical signals resulting from pairings of the biological substances in the conductive medium with the ligands coupled on the sensitive membrane are detected. The variations in electrical signals detected in said detecting step are then interpreted in order to detect said biological substances.

In an additional aspect, the present invention provides an affinity sensor for detecting biological substances present in a conductive liquid medium (LC), which comprises at least one Sc/Is/Mbs structure. The Mbs includes ligands capable of forming specific pairs with the biological substances, thereby causing a charge-effect which produces measurable variations in an electrical signal.

DETAILED DESCRIPTION OF THE INVENTION

I. General

Figure 1:
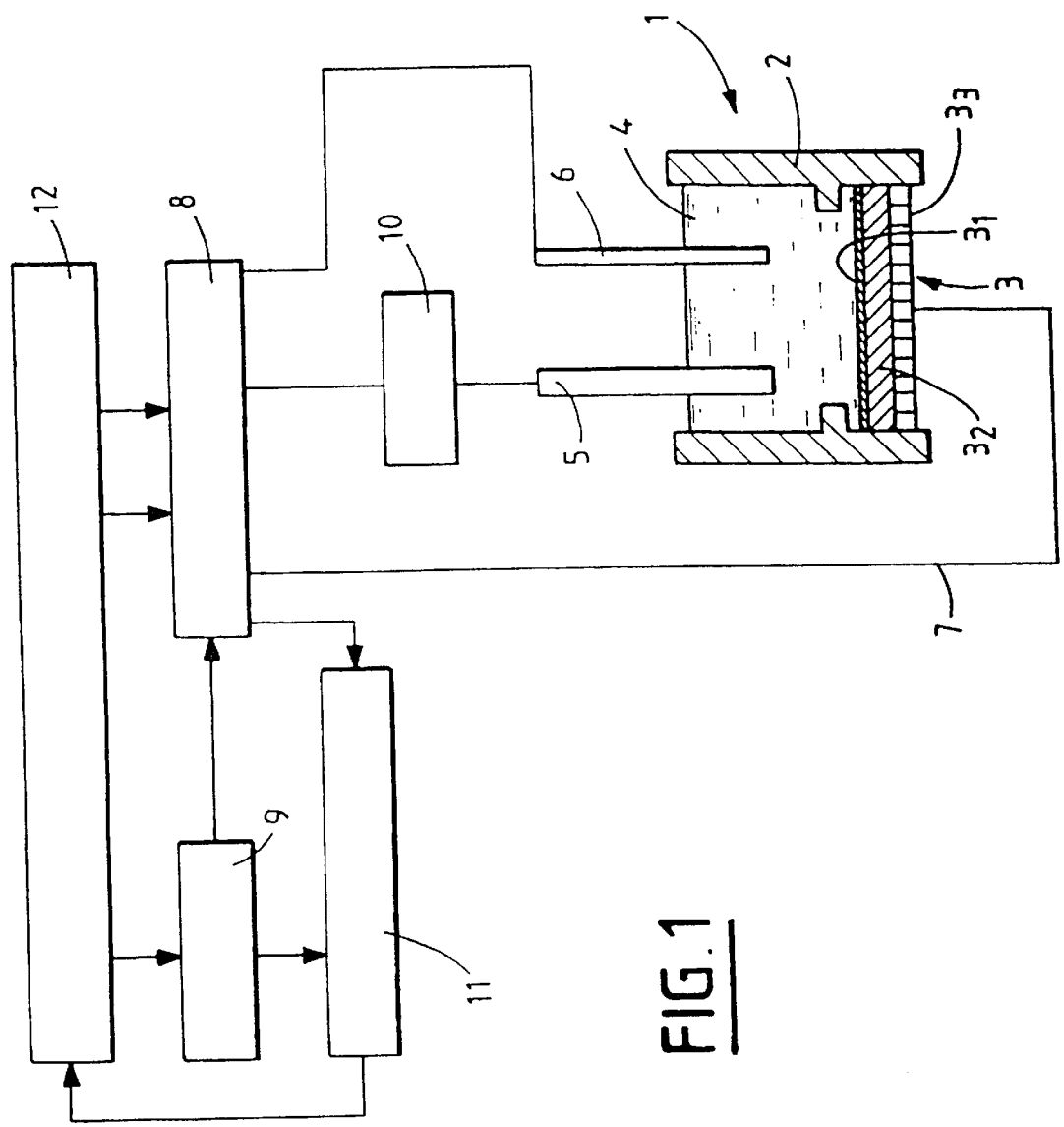
FIG. 1 is a diagrammatic representation of the electrical assembly for one embodiment of the procedure in accordance with the invention.
Figure 2:
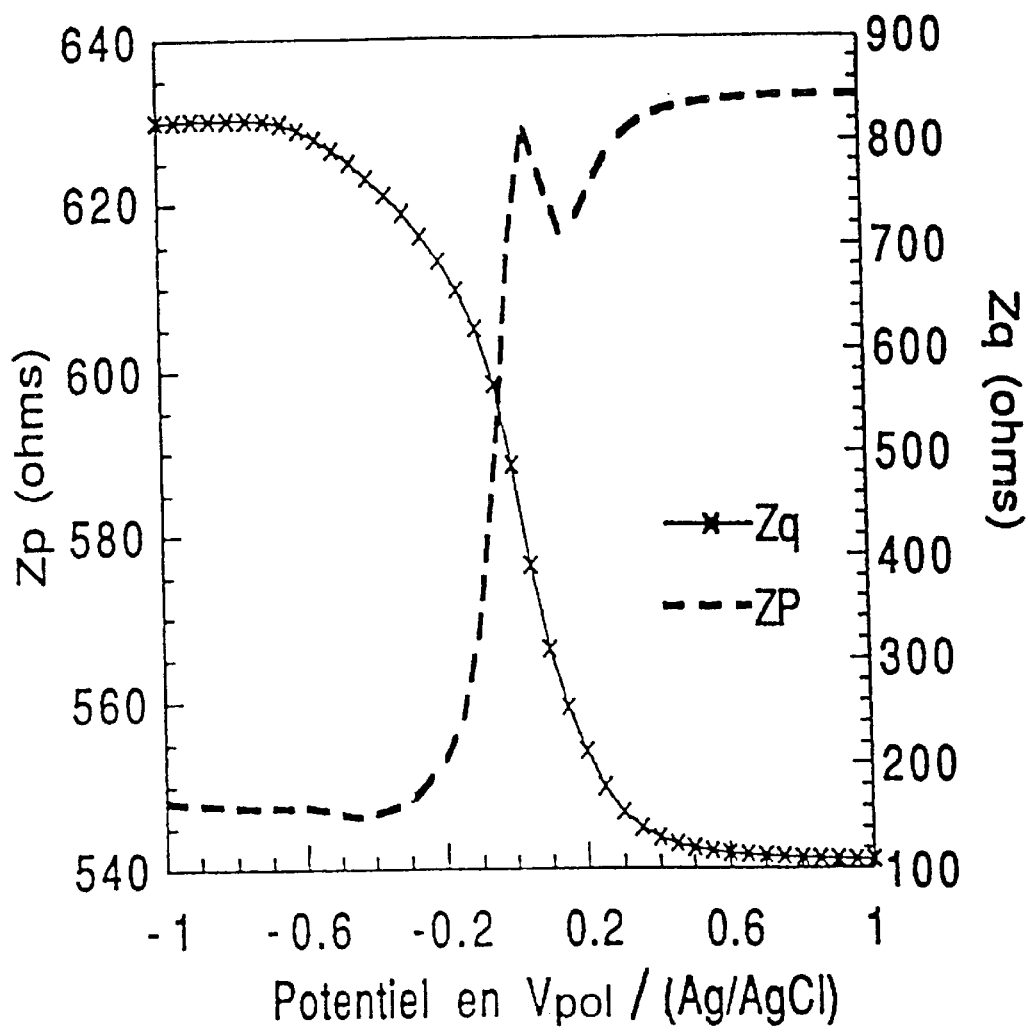
FIG. 2 represents the curves for the phase impedance Zp and the quadrature impedance Zq, as a function of the voltage $V_{pol}$, in relation to the Ag/AgCl reference electrode.

In general, the present invention provides methods and apparatuses for use in detection of chemical compounds, and particularly biological compounds. More particularly, the present invention provides methods and apparatuses for detecting binding between a biological molecule and its binding complement by detection of an electrical signal that is associated with that binding.

French patent application No. 86 06 315, filed Apr. 30, 1986, describes a method for detecting antibody/antigen interactions based upon the detection of electrical signals induced by antigen-antibody reactions in an electrically conductive liquid medium. Although not limited to immunological reactions, this patent application nevertheless only offers examples of this type of reaction. The described procedure consists of placing a liquid medium in a measurement cell and in contact with a reagent-carrier plate that contains a specific ligand which is affixed directly to one surface of a layer made of a thin isolating material, and wherein the other surface is affixed to a substrate that is capable of conducting electricity. The procedure is also characterized by measuring the capacitive and/or resistive components of the electrical impedance of the system, i.e., the liquid medium, the isolating layer, and the substrate, for a given voltage, and by comparing those components to those of a reference system, or control, which is analogous to the previous system but which does not contain any specific ligands. Any decrease in capacitance, or any variation in resistance in comparison with the reference system, indicates the presence of the substance to be detected in the liquid medium under study.

The variations in capacitance or in resistance that are involved in this measurement system are relatively small. Consequently, the sensitivity of the method is less than ideal. Furthermore, this method has thus far been limited to immunological antigen-antibody paired couples, and has not been applied to the detection, identification, or quantification of nucleotide sequences formed by hybridization, e.g., RNA, DNA, cDNA, genes, plasmids, viruses, etc.

Finally, this technique generally employs a detection system that requires a great deal of space and which is very complex to operate. As a result, this system cannot be readily miniaturized and therefore cannot be used to obtain measurements in vivo, in continuous mode, or in discontinuous mode.

It should also be emphasized that this patent application makes direct reference to another state of the art, in which use is made of the difference variations in potential, as caused by the antigen-antibody pairing at the interface between a sensitive membrane and an electrolytic solution. The effect of these variations is to cause a variation in the transverse electrical field in a field-effect transistor. The signals that are gathered are the ones obtained by means of a potentiometric measurement of the fluctuations in the gate potential or in the drain current. Such a technique (as disclosed for example by J. Janata et al. in the *Ann. New York Acad. Sci.*, 286:292 (1984)), is clearly characterizable as non-specific for the authors of patent application Ser. No. 86 06 315.

In view of this state of the art, one of the essential goals of the present invention is to provide a procedure for the quantitative and/or quantitative analysis of biological substances that is specific, highly sensitive, easy to implement, applicable to a wide variety of biological substances and particularly to (poly)nucleotide substances, inexpensive in terms of the associated capital investment, and capable of miniaturization so as to allow analytical measurements to be made in situ and/or in vivo, in a continuous or discontinuous manner.

In order to meet all of these various goals, as well as others, the present invention takes advantage of the surprising discovery that the specific pairings between macromolecules, and preferably between biological macromolecules of the antigen-antibody type, oligonucleotide-complementary oligonucleotide type, enzyme-substrate type, and others, were accompanied by a charge effect, and incidentally, by a variation in the flat-band potential $V_{bp}$ of the semiconductor in a structure that preferably comprises a multi-layer structure having semiconductor ("Sc"), isolator ("Is"), and sensitive-membrane ("Mbs") layers (indicated "Sc/Is/Mbs") form. This charge-effect phenomenon occurs at the interface between a conductive liquid medium ("LC") and a sensitive membrane which includes at least one ligand that corresponds to one member of a pair of biological compounds that are capable of forming and/or apt to form, specific coupled pairs.

Thus, in one aspect, it is a goal of the present invention to provide a procedure for the qualitative and/or quantitative analysis of substances, preferably biological substances, that are present in a conductive liquid medium ("LC"), with the aid of at least one affinity sensor which includes at least one structure which includes at least one semiconductor ("Sc") material, which is coated on one of its surfaces with at least one isolating layer ("Is"), which is in turn, affixed to at least one sensitive membrane ("Mbs"), which membrane is in contact with the conductive medium ("LC") and which sensor includes ligands that are complementary to the biological substances to be detected and which ligands are suitable for forming pairs specifically with these substances. The procedure generally comprises applying a voltage between the semiconductor and the conductive medium. The variations in the electrical signals induced by a charge phenomenon that is directly and essentially linked to the pairings of the biological substances in question with their complementary ligands included in the sensitive membrane are gathered. Variations resulting from any charge effects that may be caused by chemical reactions that are catalyzed by enzymes and in which a portion of the substances to be detected are consumed are excluded. The gathered signals are then interpreted in order to identify and/or quantify the substances in question.

This method of measurement using electrical transduction meets the desired specifications of simplicity, sensitivity, specificity, reliability and accuracy. For example, this method has been found to be remarkably effective within the context of the recognition of (poly)nucleotide sequences, by means of the hybridization of strands of nucleic acids (i.e., ligands) with strands of complementary nucleic acids that have been immobilized on the sensitive membrane of a semiconductor structure.

Although generally described in terms of nucleic acid hybridizations, it is also self-evident that the procedure in accordance with the invention is not limited to this type of nucleotide substances, but also relates to immunological (i.e., Ag/Ac) biological substances, among others.

In addition to the above-described advantages, the methods of the present invention also have the advantage of being reversible. In fact, it is easily possible to uncouple the complementary species that reacted specifically at the sensitive membrane of the semiconductor structure. Thus, the sensitive membrane can be regenerated after each use, and can be regenerated a number of times.

In brief, the value of the methods of the present invention lies in the ability to detect and/or quantify biological substances by making use of their specific affinities. This affinity-based analysis method does not require reactive intermediaries, specific markers, or enzymatic reactions.

Earlier, such advantageous results were difficult to predict, as it was assumed in the art that immunological coupling reactions, enzymatic complexation reactions, or even nucleic acid hybridization reactions, did not involve the generation of any charge-effect phenomena that were significant or that could be utilized analytically. The present invention completely reverses this technical prejudice, and in particular makes it possible to detect and quantify nucleotide sequences, for example, in order to detect genetic diseases; to detect and characterize viruses, bacteria, and parasites, and to create genetic maps.

In particularly preferred aspects of the present invention, the specific pairings that are exploited correspond to at least one of the following biochemical mechanisms nucleotide hybridization, and immunological coupling.

II. Detection Methods

In a first aspect of the methods of the present invention, the electrochemical impedance measurement is utilized to characterize the semiconductor/isolator/sensitive membrane/conductive liquid structures and, in particular, to determine the induced charge effect.

In order to do so, a potentiostatic measurement method is implemented that utilizes at least three electrodes: (1) at least one working electrode consisting of the semiconductor/isolator/sensitive membrane structure; (2) at least one reference electrode that forms the reference system (for example, of the Ag/AgCl type); and (3) at least one counter-electrode.

A polarization voltage ("$V_{pol}$") is applied to the working electrode, with the polarization voltage being continuous in relation to the reference electrode, which is immersed in the electrolytic medium. A sinusoidal electrical modulation is superimposed on the voltage $V_{pol}$. A measurement is made of the voltage ("V") between the working electrode and the reference electrode, and of the current ("I") passing through the working electrode. The phase impedance ("Zp") and the quadrature impedance ("Zq") are then calculated. The Zp and/or Zq curve(s) are drawn up as a function of $V_{pol}$ and the shift or displacement of these curves (or curve) parallel to the axis of the potentials is monitored. The shift or displacement corresponds to the variations in the electrical signals as induced by the charge effect resulting from the specific pairings of the biological substances to be analyzed with their complementary ligands that are present in the sensitive membrane, and as gathered in accordance with the procedural methodology described above.

The shift or displacement of the Zp and/or Zq curve, as a function of $V_{pol}$ is preferably monitored by means of the flat-band potential $V_{bp}$ of the semiconductor, which is deducted from the said curve (or curves).

The continuous polarization voltage $V_{pol}$ advantageously varies within a range that contains the depletion zone of the semiconductor, and preferably within the range from −3 to +3 V, and even more preferably within the range from −1.5 to +1.5 V.

With regard to the superimposed electrical sinusoidal modulation, this modulation is preferably located within a range of average frequencies ranging from 50 to 500 KHz, and preferably from 100 Hz to 100 KHz. This modulation is also advantageously of low amplitude, e.g., between 1 mV and 100 mV.

For greater convenience, a current/voltage converter can be utilized, which can be switched electronically and allow measurements to be made of either the voltage ("V") that is presence between the reference electrode and the working electrode, or the current ("I") passing through the structure.

Advantageously, these two magnitudes are analyzed in phase (i.e., the real or actual portion) or in quadrature (i.e., the imaginary portion), thanks to a synchronous detection procedure based on the frequency of the sinusoidal modulation provided by the generator.

In a preferred embodiment of the invention, the operations consisting of the driving and acquisition of the measurements are performed by means of a desktop computer, which performs the impedance calculation in accordance with Ohm's law, in a known manner.

This particular implementation of the procedure in accordance with the invention, through the measurement of impedances, makes it possible to trace the phase impedance (Zp) curves and the quadrature impedance (Zq) curves as a function of the voltage (V). The shift or displacement of the impedance curves in a direction parallel to the axis of the potentials caused by the biological recognition effect, among others, corresponds to the variations in potential of the flat bands in the Sc/Is/Mbs structure.

The flat-band potential $V_{bp}$ can be determined in accordance with the quadrature impedance curve, through the application of the well-known Mott-Schottky relationship.

The impedance measurements also make it possible to evaluate the electrical signals induced by the biological interactions taking place at the surface of the structure.

In a second aspect, use is made of the field effect induced by the variations in the surface charge caused by the pairing of the complementary biological substances. This field effect, which is located in the surface region of the underlying semiconductor, causes a change in the concentration of free-charge carriers in this region, and consequently, a change in the transconductance of the channel of a field-effect transistor, which is utilized in accordance with this second aspect of the invention.

Thus, the electrochemical sensor utilized in this aspect of the present invention generally comprises a field-effect transistor whose gate, which is in contact with the electrolytic quantification medium, is formed by the sensitive membrane. This transistor is associated with at least one reference electrode that is also immersed in the conductive liquid medium. The signals that are induced by the reaction of the biological substances with the sensitive membrane, and which are measured, consist of the variations in the current and/or in the voltage.

In this aspect of the methods of the invention, with the use of a field-effect transistor, the voltage applied between the semiconductor structure and the reference system may be generated by any number of a variety of known appropriate voltage sources.

The sensitive membrane aspect of the field-effect transistor typically includes at least one specific ligand that is capable of recognizing selectively the biological substance to be detected.

Such sensors may be referred to as "BIOFETs". And, in the case in which the biological species in question consist of nucleic acids or analogous substances, the sensors in question may be "GENFETs" or, in the case of antigen-antibody pairings, "IMMUNOFETs".

The electrical signals measured by the "BIOFET" (or, for example, by a "GENFET" and/or by an "IMMUNOFET") may be obtained, for example, using the following procedure: A constant value is imposed on the potential $V_{ds}$ between the drain and the source. The drain current is kept constant, at an index value, with the potential between the reference and the source, $V_{rs}$, being adjusted. A measurement is made of the variations in $V_{rs}$ in response to the interactions between the sensitive membrane and the quantification medium.

Following this procedure, the potential $V_{rs}$ is similar to the $V_{gs}$ potential between the gate and the source of the field-effect transistor.

In an alternative method, it is perfectly possible to implement the inverse procedure, i.e., to impose and maintain a constant value for the potential $V_{gs}$ or current $V_{rs}$, and to measure the current and/or the variations in the drain current.

In a variation of the invention, it is possible to dramatically reduce or eliminate the non-specific responses by implementing a differential measurement method, in accordance with which an integrated reference is provided that consists of at least one semiconductor ("Sc")/isolator ("Is") structure that does not include a sensitized membrane, and which integrated reference also constitutes at least one other field-effect transistor that is utilized as a reference (REFET) in a conductive liquid medium ("LC"). In parallel with the latter component, an "Sc"/"Is"/"Mbs" measurement structure (FET) is provided in which the sensitive membrane includes specific reactive elements (i.e., ligands) that are in contact with the conductive liquid medium ("LC"). The output signal that is gathered is formed by the difference in the responses provided by the reference and by the Sc/Is/Mbs structure placed under the same conditions.

As will be clear upon reading the instant disclosure, the invention is not limited to the foregoing embodiments, but also can include all analogous measurement methods that can be envisioned and that are based on the recognition of the variation in the flat-band potential of an Sc/Is/Mbs structure that includes a sensitive region that is capable of, and suitable for, reacting specifically with biological substances in a conductive liquid medium (LC).

The biological substance in question include, inter alia, any of the following substances: a polynucleotide sequence (e.g., RNA, DNA, a gene, a plasmid, or any other genetic material), an antigen, hapten, antibody, or, generally speaking, any species that is a member of a pair consisting of a macromolecular biological substance and its specific complement. Examples of such specific pairs include antigens and antibodies; haptens and antibodies; cDNA and DNA; cDNA and RNA; poly-dT-mRNA; eukaryotes and glycoconjugated lectin; cell (or microorganism) markers and cells (or microorganisms); and the tissular HcG receptor and $T_3$ TGB (thyroxin binding protein).

The methods of the invention typically begin with the immobilization of at least one type of these reactive biological species in order to form the sensitive membrane. This step can take place directly on the isolating layer, or, alternatively, can be performed with the aid of an intermediate material (e.g., a spacing compound), that is affixed adhesively to the isolator and that is suitable for receiving the specific biological ligands, either by means of a physical link (such as adsorption and/or absorption) or by means of a chemical bond (such as a covalent bond).

In accordance with the invention, it is perfectly reasonable to envision the provision of a heterospecific sensitive membrane that is made of biological species of different natures, all of which are capable of, and suitable for, reacting with their complements.

In order to improve the sensitivity of the measurement of the device or method, the sensitive pairing membrane should be as fine as possible or even monomolecular.

The conductive liquid medium used may generally consist of any buffer solution that is compatible with the biological substances in question. The conductivity of this liquid medium is advantageously equivalent to that of an aqueous NaCl solution whose concentration may range from 0.005M to 3M, and is preferably on the order of 0.1M.

The pH of the liquid medium typically may be between 0 and 12, and is preferably between 6 and 8, and advantageously is on the order of 7, in order to encourage bioaffinity pairings.

The non-specific interactions, which take place by means of ion exchanges or as a result of hydrophobic reactions, may be prevented in whole or in part with the aid of a buffer with the appropriate ionic strength.

The measurement temperature may advantageously be between 0 and 50° C. It is preferably on the order of 37° C., in order to encourage the biochemical reactions in question.

III. Detection Apparatuses

The structure that lies at the heart of the present invention advantageously consists of a multi-layer structure consisting successively of the following components: at least one semiconductor material (Sc); at least one layer of a dielectric blocking material (Is), consisting for example of a thin layer of oxide that prevents any faradic phenomena; and at least one sensitive membrane (Mbs) that includes at least one biospecific pairing ligand. This structure is associated with a conductive liquid medium (LC) that contains the substances to be quantified, detected, or identified.

The return to thermodynamic equilibrium that occurs after the imposition of a continuous voltage $V_{pol}$ on this structure, in comparison with a reference (polarization), results in the adjustment of the Fermi levels of the semiconductor in the conductive liquid medium. This adjustment involves a distribution of the charges within the interior of the semiconductor, and, more specifically, in its space-charge zone (i.e., the charge effect), so as to ensure the electrical neutrality of the semiconductor. This phenomenon leads to the appearance of the curvature of the semiconductor band. The flat-band potential $V_{bp}$ is the potential that must be applied to the system (in comparison with a potential reference electrode that is immersed in the liquid medium), in order for the curvature of the semiconductor band to be null.

To the extent to which the electrical charge varies at the surface of the semiconductor as a result of the effect of the pairing of the biological species (i.e., the ligand) and the complementary biological species, this variation involves a natural compensation for this change in the charge through a reorganization of the distribution of the charge within the space-charge zone. Consequently, this compensation creates a new electrical field in the structure (and thus a new charge effect), induces a new band curvature, and as a result, a change in the band potential $V_{bp}$ of the semiconductor. This change involves a variation in the electrical signals, among other things, that can be detected and collected as an expression or indication of the biospecific pairing of the ligand and the complementary biological species to be analyzed, as described above.

Accordingly, in another aspect, the present invention provides an electrochemical sensor for the implementation of the detection methods described above. The sensor includes at least one Sc/Is/Mbs structure, in which the Mbs includes ligands that are suitable for forming specific pairs with substances, which are preferably biological substances, in order to cause a charge-effect phenomenon, which phenomenon in turn gives rise to measurable variations in electrical signals, in such a way that variations in the potential of the $V_{bp}$ semiconductor band or in the field effect modify the transconductance of the channel of a FET (field-effect transistor).

The semiconductor/isolator/membrane (Sc/Is/Mbs) structure of this sensor consists respectively of silicon, silicon dioxide, and the ligand(s), which are affixed to the silicon dioxide, preferably by means of spacing compounds as described above.

The affinity sensors in accordance with the invention may be characterized by their inclusion of a specific pairing mode of the nucleotide hybridization type, so as to allow the formation of a GENFET, and/or of the immunological coupling type, so as to allow the formation of an IMMUNOFET.

In practice, these sensors advantageously consist of heterostructures formed by an n-type or p-type silicon substrate that has at least one ohmic contact located on at least one of its surfaces, and that is covered on the surface opposite that surface, with at least one $SiO_2$ film, whose thickness is between 10 and 500 angstroms, and preferably between 50 and 150 angstroms, and even more preferably, on the order of 100 angstroms thick. The oxide film that forms the isolating layer is adhesively affixed to the sensitive membrane, by means of its surface opposite the surface that is adjacent to the semiconductor. The semiconductor may consist of at least one layer of an intermediate material that is affixed, preferably by means of a covalent bond, to the $SiO_2$ isolating layer. This intermediate layer serves as an immobilization substrate for the ligand for at least one biological species whose reactive complement is to be detected, identified, or quantified. The intermediate layer may, for example, consist of at least one functionalized silane. As described above, the ligand may, for example, consist of a strand of RNA, DNA, or any other polynucleotide sequence.

After nucleotide hybridization or immunological coupling has been performed, the sensitive membrane of the electrochemical sensor in accordance with the invention may be regenerated through the implementation of a denaturation stage. The latter stage is preferably implemented by means of thermal treatment in the presence of a solvent, which advantageously consists of deionized water.

In accordance with the invention, the electrochemical sensor, as adapted for use in the second aspect of the methods described above, advantageously includes at least one field-effect transistor that can be powered by at least one electrical power source.

The procedure that implements the sensor in accordance with the invention makes it possible to envision the detection and/or identification and/or quantification of sequences of nucleic acids (e.g., DNA or RNA) or of any other genetic units consisting of these elementary sub-units, i.e., nucleotides. This characteristic can be particularly worthwhile for the detection of genetic diseases (i.e., anomalies in the genome), for the detection and characterization of viruses, bacteria, or parasites, or in the creation of genetic maps.

The analytical technique in accordance with the invention may also be applied to antigen/antibody systems, to the extent to which the pairing of each the ligands and of its reactive complement, which pairing characterizes these systems, generates a field effect and a variation in the potential of the flat bands in an Sc/Is/Mbs structure immersed in an LC medium that contains the substances to be analyzed.

FIG. 1 illustrates a schematic representation of one embodiment of an electrochemical sensor according to the present invention. Specifically, the complete electrochemical sensor shown in FIG. 1 includes a measurement container [1] that consists of walls [2] and a bottom [3] made from the Sc/Is/Mbs structure. The said container [1] contains a conductive liquid medium [4], into which are immersed a reference electrode [5] (consisting of saturated Ag/AgCl) and a counter-electrode [6] made of platinum.

The Sc/Is/Mbs structure or the bottom [3], at the bottom of the container [1], forms the working electrode and includes three superimposed layers, designated by references [$3_1$] to [$3_3$], in order from the inside of the container toward the outside. The inner layer [$3_1$] consists of the sensitive membrane that includes the specific ligand or ligands, in immobilized form. The middle layer [$3_2$], which corresponds to the $SiO_2$ isolator, and the outer layer [$3_3$] are made of the p-doped silicon semiconductor. An ohmic contact is provided, which is located on the outer surface of this layer [$3_3$] and which is connected to a conductive wire [7]. The measurement circuit also includes an adjustable (rapid potentiostat) power-supply module; a function generator [9] that enables the application of a sinusoidal electrical modulation with a low amplitude and a medium frequency; a current/voltage converter [9]; a voltage tracker [10], and synchronous detection means [11]. The functioning of the entire set of these components is managed by a computer [12].

The present invention is further illustrated by the following examples. These examples are merely to illustrate aspects of the present invention and are not intended as limitations of this invention.

IV. EXAMPLES

Example I

Impedance Measurement with a Sensor Incorporating an Oligonucleotide Sensitized Membrane 1. Manufacture of the Sensor Apparatus A sensor apparatus as shown in FIG. 1 was produced as follows:

The conductive solution (designated by reference [4] in FIG. 1) was prepared by mixing 10 mM of Tris HCl (tris[hydroxymethyl]-aminomethane hydrochloride) with 10 mM of Tris base (tris[hydroxymethyl]-aminomethane) and 50 mM of NaCl. This solution was used as a conductive medium for the impedance measurements and as a rinsing solution during the preparation of the structures.

The heterostructures that formed the working electrode [3] were formed from a p-Si substrate (layer [3], with an ohmic contact on the outer surface) covered with a film of $SiO_2$ 100 angstrom units thick (layer [$3_2$]). The structures were degreased by means of successive immersions for 10 minutes in a boiling bath, first in acetone and then in isopropanol.

The $SiO_2$ surface was hydrated by means of immersion in sulfochromic acid for 5 minutes, followed by careful rinsing, first with deionized water and then with the Tris buffer solution. The hydroxylated Si/$SiO_2$ surface was then covered with APTS (aminopropyltriethoxysilane) diluted to 5 percent in water and left at room temperature for one hour. The coated surface was then rinsed with the Tris solution. The APTS formed a part of the membrane, which was then sensitized by immobilizing the ligand consisting of single stranded DNA. The immobilization of the single stranded DNA (i.e., dT oligonucleotides with nitrogenous thymine bases, for trial No. 1) was achieved utilizing a bromosuccinimide method (cf. Keller, Anal. Biochem. 170:441 (1988)).

The DNA solution was prepared by adding 20 $\mu$l of 0.01M N-bromosuccinimide to 1 ml of a 1M $NaHCO_3$ containing the DNA at a concentration of 1 mg/ml, and then allowing the reaction to proceed for 15 minutes at 0° C. One drop of this solution was placed on the layer of APTS, which was then allowed to dry at room temperature overnight.

2. Measurements

A) Impedance Measurements Before Hybridization (Trial No. 1)

The electrical measurements were made after each stage in the preparation of the heterostructure.

The curve for phase impedance is indicated as Zp whereas the curve for quadrature impedance is indicated as Zq. There are three polarization ranges, which correspond to the various types of behavior of the underlying semiconductor, i.e.: an inversion situation [V<−0.4 V/(Ag/AgCl)]; a depletion situation [−0.6 V<V+0.6 V/(Ag/AgCl)]; and an accumulation situation [V>+0.6 V/(Ag/AgCl)]; for the charges at the interface.

B) Monitoring of Hybridization by Means of Impedance Measurements (see FIG. 3) (Trial No. 2 to Trial No. 6)

Hybridization was carried out using a solution containing 1M $NaHCO_3$ and the single stranded complementary oligonuucleotides, at a concentration of 0.1 mg/ml. Denaturation of the hybridized oligonucleotides, i.e., the regeneration of the membrane after hybridization, was achieved by boiling the samples for 20 minutes in deionized water.

A first series of highly reproducible impedance measurements was made on sensors whose Sc/Is/Mbs structure included a bare membrane (Trial No. 2). A second series of measurements of Zq was made following the immobilization of the dT oligonucleotides (Trial No. 3) ($Sc/Is/Mbs_1$). A third series of measurements was made after hybridization with the complementary oligonucleotides. A fourth measurement was made after denaturation (Trial No. 5), and a fifth series of measurements was made after rehybridization (Trial No. 6). These measurements were made at a sinusoidal electrical modulation frequency ("F") of 100 KHz.

Figure 3:
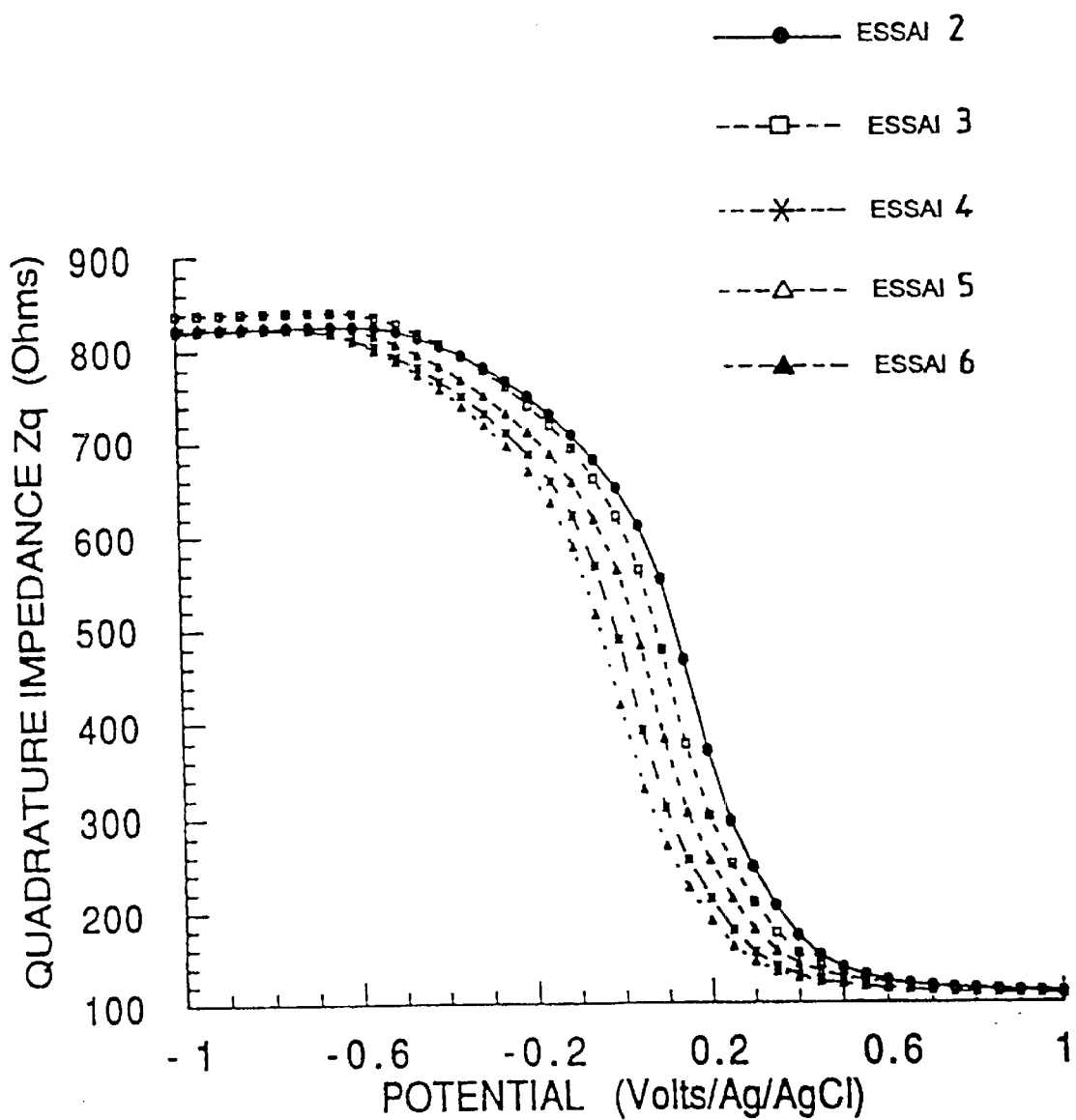
FIG. 3 represents curves $Zq=f(V_{pol})$ under various different experimental conditions for ex-situ hybridization.

Hybridization resulted in a shift or displacement of the curves in relation to the axis of the potentials on the order of 100 mV (see FIG. 3). This shift or displacement was measured after an ex-situ hybridization, in which the hybridization stage was performed on the sample outside the measurement cell described in FIG. 1.

The translation of the Zq ($V_{pol}$) curves, as well as that of the Zp ($V_{pol}$) curves, along the axis of the potentials corresponds to a variation in the flat-band potential $V_{bp}$, which in turn indicates the presence of the field-effect phenomenon at the surface.

These results show that the biological signal (i.e., hybridization of the complementary strands) may be manifested in the form of a measurable physical magnitude (i.e., the variation in $V_{rs}$), thanks to the use of a semiconductor transducer. Reversibility was also tested, inasmuch as, when the structure was denatured (i.e., through the separation of the complementary strands from the immobilized strands, in Trial No. 5), the Zq ($V_{pol}$) curves returned to their initial position (i.e., their position prior to hybridization (Trial No. 3)). It could also be verified that the structures could be hybridized and denatured five times in a row without any loss in performance.

C) Monitoring of Hybridization (in situ) by Means of Zq Impedance Measurements (Trial No. 7 to Trial No. 12)

The ligand that was immobilized on the sensitive membrane of the sensor was a dT oligonucleotide. The hybridization was performed in situ by pouring 20 μl of dA oligonucleotide contained in 12 ml of Tris HCl, into the measurement receptacle [1] containing the medium [4]. A first series of measurements of Zq was made with the non-hybridized dT oligonucleotides of the sensitized membrane (Trial No. 7). Five other series of measurements of Zq were made at various times after the addition of the solution containing the complementary species to be detected, i.e., the dA oligonucleotide, as indicated below:

Trial No. 8=0 hours
Trial No. 9=2 hours
Trial No. 10=3 hours
Trial No. 11=6 hours
Trial No. 12=24 hours The Zq measurements were made at a frequency F=20 KHz.

Figure 4:
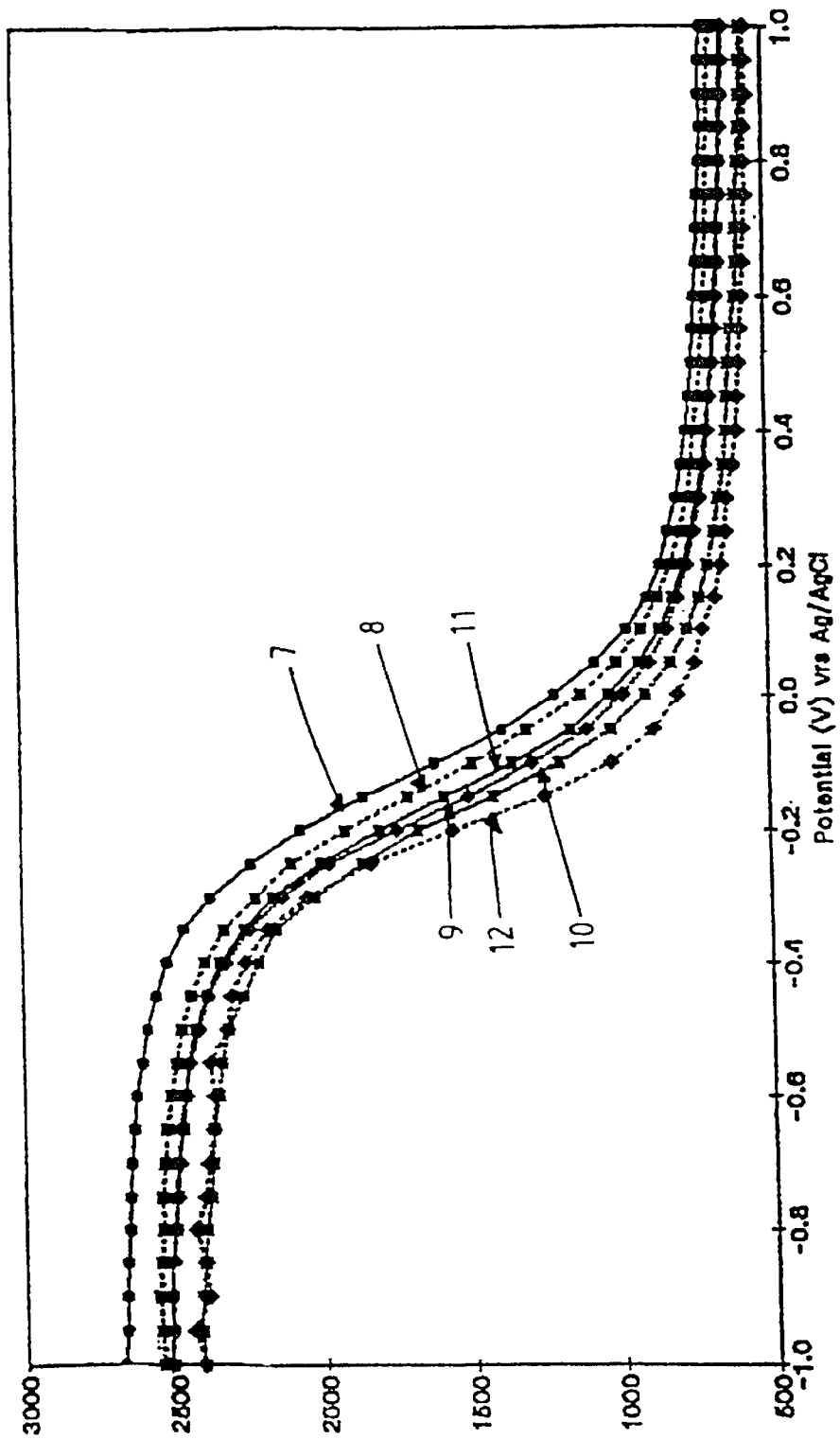
FIG. 4 represents curves f(Vpol) that correspond to the monitoring of the in-situ hybridization of an oligonucleotide with its complement.

FIG. 4 shows the shape of the Zq=f (Vpol) curves obtained. In particular, the hybridization procedure produced a shift or displacement of the curves in relation to the axis of the potentials, on the order of 120 mV (Δ $V_{bp}$).

Figure 5:
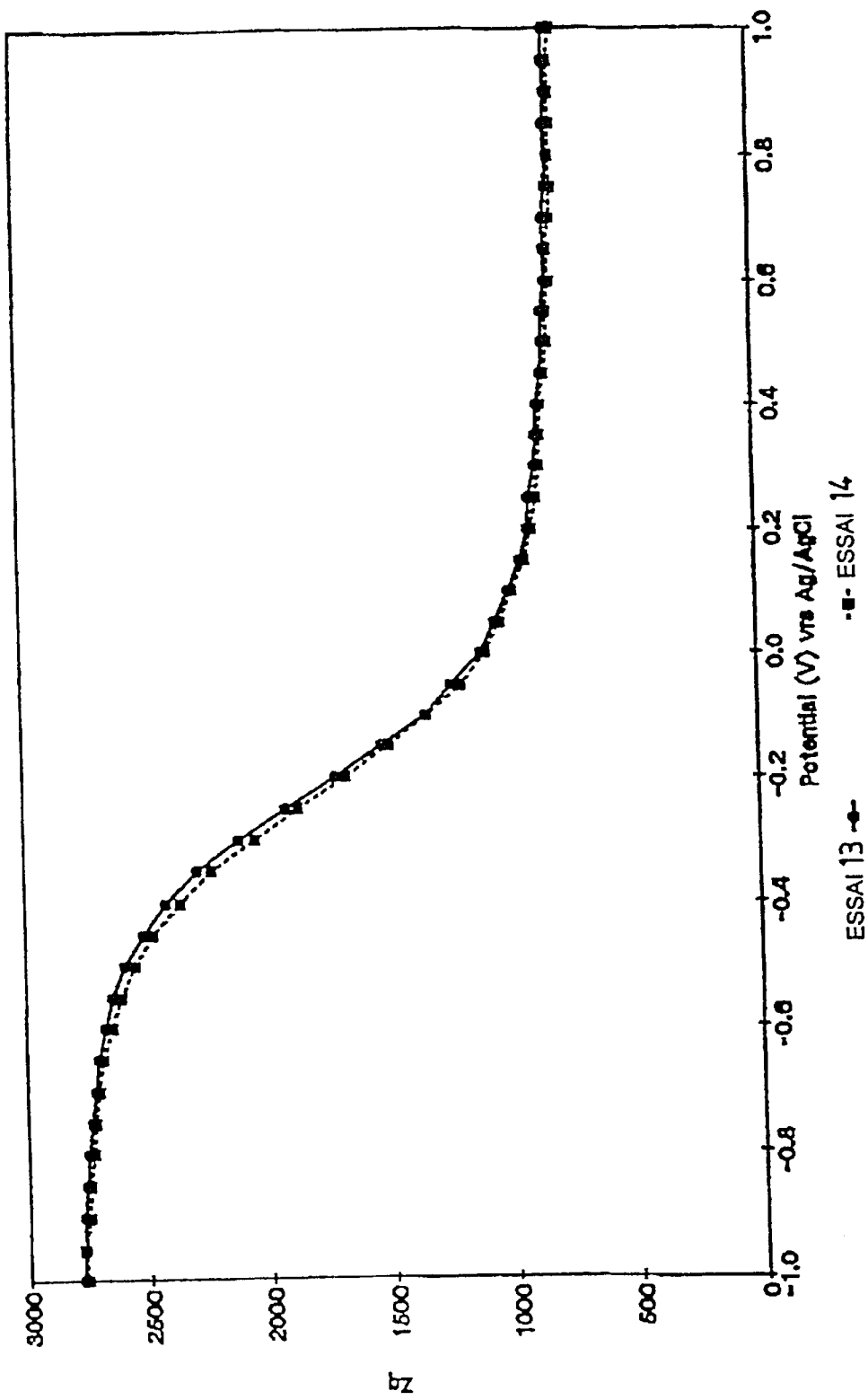
FIG. 5 represents two curves Zq=f(Vpol) for immobilized ligands that cannot be paired with the biological species present in the electrolytic liquid medium.
Figure 6:
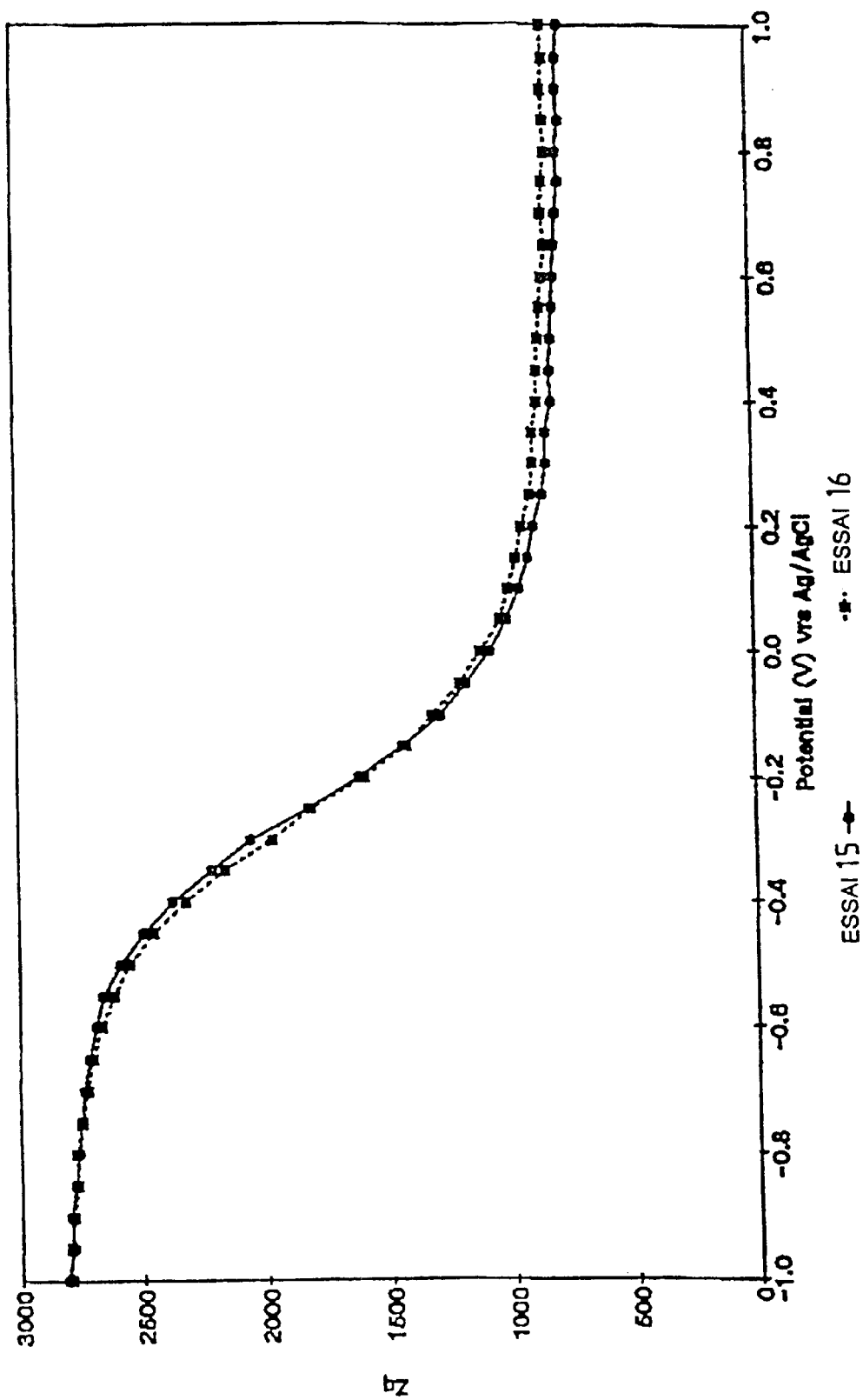
FIG. 6 represents diagrammatically a BIOFET (i.e., a GENFET) in accordance with the invention.

D) Zq Impedance Measurements Made after the Sensitive Membrane of the Sensor was Placed in the Presence of Polynucleotide Strands that were not Complementary to the Immobilized Oligonucleotide Ligands The immobilized ligands consisted of dT oligonucleotides (see FIG. 5). Polynucleotide dC ligands were added to the measurement receptacle containing the sensor, under the same conditions as in trials 7 to 12. A first series of measurements was made before the incorporation of the dC polynucleotides (Trial No. 13). A second series of measurements was made after the incorporation of the dC polynucleotides (Trial No. 14). FIG. 5 shows the shape of the resulting curves. In this assay, the immobilized species consisted of dT polynucleotides (see FIG. 6). Polynucleotide dC ligands were added to the measurement receptacle containing the sensor, under the same conditions as in trials 7 to 12. A first series of measurements was made before the incorporation of the dC polynucleotides (Trial No. 15). A second series of measurements was made after the incorporation of the dC polynucleotides (Trial No. 16). FIG. 6 shows the shape of the resulting curves. The specificity of the signal was verified, inasmuch as no shift or displacement of the $\Delta V_{pol}$ curves was observed during the 24 hours following the introduction of the dC polynucleotides into the measurement cell. This non-observation logically corresponds to the impossibility of any pairing between the dT oligonucleotides and the dC polynucleotides.

The results obtained and the observations made within the context of the first embodiment of the implementation of the procedure in accordance with the invention, as described in Example I, led the applicant to envision the revelation of the specific and selective pairing phenomenon between the immobilized ligand of a biological species and its complement, with the aid of a transducer of the field-effect transistor type (i.e., a BIOFET, in the form of a GENFET or an IMMUNOFET).

Figure 7:
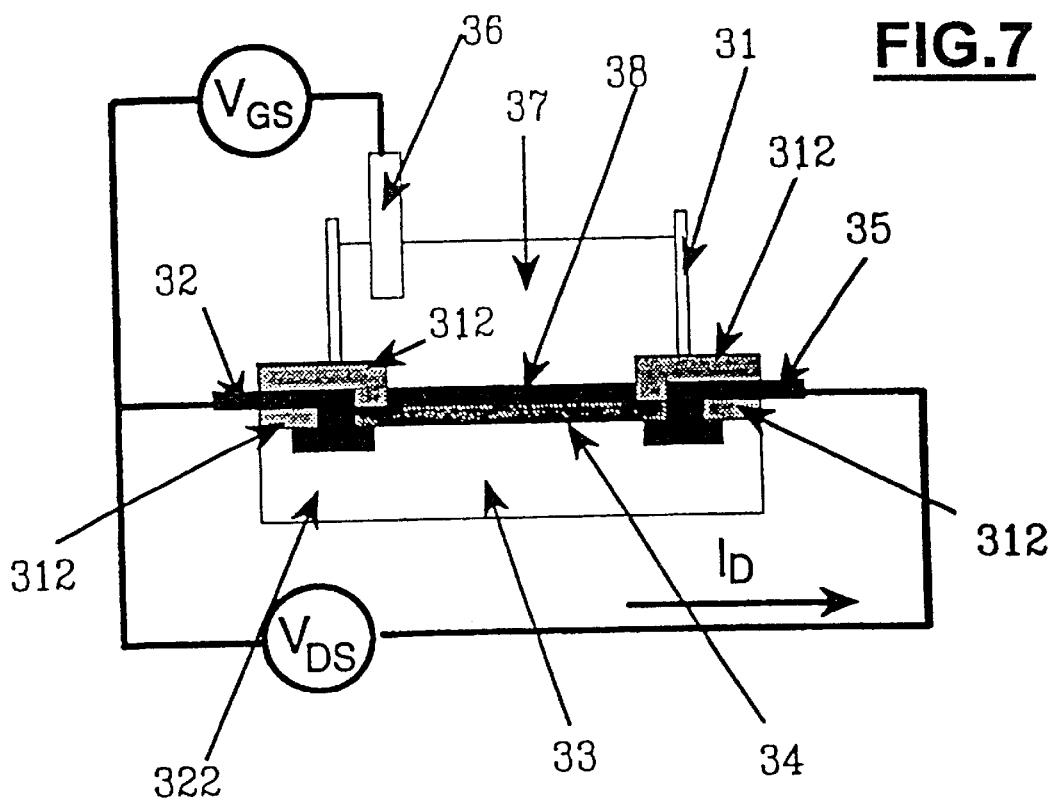
FIGS. 7 through 10 represent the response curves $\Delta V_{gs}$, as measured for GENFETs of the type shown in FIG. 6, under various different experimental conditions for the hybridization of the oligonucleotides.

The attached FIG. 7 represents a schematic cross-sectional view of a GENFET in accordance with one embodiment of the invention.

Traditionally, this GENFET includes a source [32]; a p-type silicon substrate [33]; an isolator [34]; a drain [35] and a source [32] that contain no metal contacts; a reference electrode [36]; a conductive liquid medium [37] contained in a receptacle [31]; a sensitive membrane [38]; and an encapsulating shell [312].

In this experimental assembly for the measurement of the output signal, a constant potential value is applied between the drain and the source ($V_{ds}$), and an amplifier keeps the drain-source current constant at an index value, by adjusting the $V_{gs}$ potential between the source and the reference electrode.

Thus, the response of the sensor, as read directly in millivolts, consists of the measurement of these variations (i.e., $\Delta V_{gs}$). It is directly linked to the concentration of the biological species to be detected in the solution.

Example II

Monitoring a Hybridization Operation with the Aid of the GENFET Transistor

Figure 8:

FIG. 8 shows the response obtained with the "GENFET" in the case where the sensitive element is the dT polynucleotide, after the addition (as indicated by the arrow

[F]) of 10 μg of a solution containing the dA polynucleotide (with the concentration of the dA polynucleotide in the latter solution being 2×10$^{-4}$ g/ml). The conditions for this trial (i.e., Trial No. 17) are listed below:

Working solution: Tris buffer Temperature: 25$_i$ C. Volume: 5 ml

Injected solution: dA polynucleotide DNA (1 mg/ml in 1M NaHCO$_3$) Injected volume: 10 μl The maximum amplitude of the signal was 120 mV, and this amplitude was stabilized after 8 hours. After one hour, 50% of the signal had been obtained. This amplitude corresponded to the shift in the potential of the flat bands, as measured by the impedance values on Sc/Is/Mbs structures in the presence of the same concentration of dA polynucleotides. This quantification range is mentioned for illustrative purposes. The limit of detection can be improved, particularly through the optimization of the immobilization of the recognition elements.

There was no change in the value of $\Delta V_{gs}$ when the GENFET was in the presence of a solution that contained the same concentration of non-complementary strands (i.e., dC polynucleotides). The subsequent addition of a controlled quantity of dA polynucleotides to the solution did cause a variation in the value of $\Delta V_{gs}$.

In this example, it could be seen that the quantification range for this method lay between 10$^{-4}$ and 10$^{-8}$ g/ml of the biological substance to be quantified.

Example III

Figure 9:
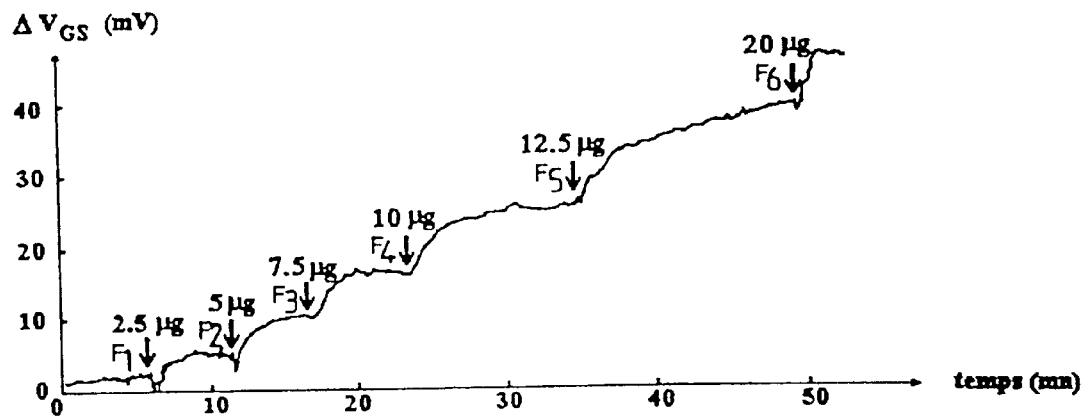

In Situ Response of a GENFET to the Addition of Various Amounts of the Species to be Detected FIG. 9 shows the response obtained for a GENFET in which the sensitive element is the dT polynucleotide. The successive additions of controlled quantities of a dA polynucleotide solution in NaHCO$_3$ (at 1 mg/ml) produced a variation in the value of $\Delta V_{gs}$. Arrows F1 to F6 correspond respectively to the addition of 2.5 μg, 5 μg, 7.5 μg, 6 μg, 12.5 μg, and 20 μg of the dA polynucleotide solution. The working solution consisted of 1M NaHCO$_3$.

Example IV

Figure 10:
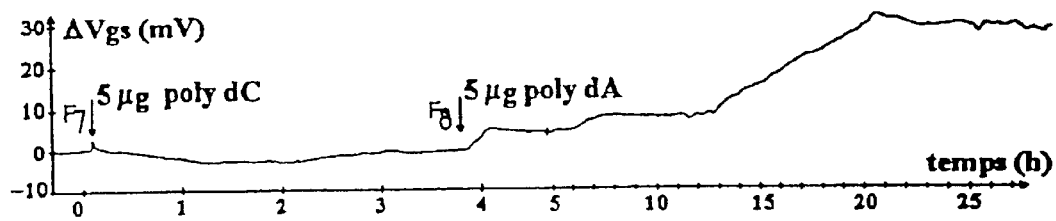

In Situ Response of a GENFET to the Successive Introduction of Two Different Species, One of which is not Specific for this Sensor, and the Other of which Corresponds to the Complements of the Species Immobilized on the GENFET FIG. 10 shows the response obtained with a GENFET whose sensitive element is the dT polynucleotide. The experimental conditions were as indicated below:

Injected solutions:
1) dC polynucleotides in NaHCO$_3$ (at 1 mg/ml)
2) dA polynucleotides in NaHCO$_3$ (at 1 mg/ml)

Temperature: 37° C.

Working solution: Tris buffer, at a pH of 7.1

The introduction of biological species (dC polynucleotides, as indicated by arrow F7 (5 μg)) that were not specific for this GENFET did not produce any variation in the value of $\Delta V_{gs}$. The addition of complementary species (i.e., dA polynucleotides, as indicated by arrow F6 (5 μg)) did cause a variation in the value of $\Delta V_{gs}$.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method for detecting a biological substance present in a conductive liquid medium which comprises providing an affinity sensor which includes an insulator member having opposed surfaces, a semiconductor member attached to one of said opposed surfaces and a sensitive membrane on the other surface of said insulator member, said sensitive membrane crying a coupling substance which will couple with the biological substance, positioning the affinity sensor so that the sensitive membrane with said substance thereon contacts said conductive liquid medium and said semiconductor member is out of contact with said liquid medium; applying a voltage between said semiconductor member and said liquid medium; and detecting variations in electrical signals which result from pairings between said coupling substance and biological substance in said medium.

2. The method of claim 1, wherein the sensor further comprises at least one working electrode consisting of the semiconductor/isolator/sensitive membrane structure, at least one reference electrode that forms a reference system, and at least one counter-electrode;

the applying step comprises applying a polarization voltage $V_{pol}$, to the working electrode, the polarizatioll voltage being continuous in relation to the reference electrode immersed in the conductive medium, superimposing on the voltage $V_{pol}$, a sinusoidal electrical modulation; and the detecting step comprises measuring a voltage between the working electrode and the reference electrode, and a current passing through the working electrode, calculating a phase impedance Zp or the quadrature impedance Zq, plotting the Zp or Zq curve as a function of $V_{pol}$, and monitoring a shift of the curve, with the shift corresponding to the variations in the electrical signals, as induced by the charge effect resulting from the pairings of the biological substances with the coupling substance.

3. The method of claim 1, wherein the pairings comprise a reaction selected from the group consisting of nucleotide hybridization, and immunological coupling.

4. The method of claim 2, wherein the pairings comprise a reaction selected from the group consisting of nucleotide hybridization, and immunological coupling.

5. The method of claim 2, wherein the shift in the Zp or Zq curve is monitored by monitoring a flat-band potential ($V_{bp}$) of the semiconductor material, which is deduced from the curve.

6. The method of claim 2, wherein the polarization voltage varies within a depletion range of the semiconductor material.

7. The method of claim 2, wherein the polarization voltage is from −3 to +3 V.

8. The method of claim 2, wherein the polarization voltage is from −1.5 to +1.5 V.

9. The method of claim 1, wherein:

the affinity sensor includes at least one transducer element formed by at least one field-effect transistor having a gate in contact with the conductive medium, the gate formed by the sensitive membrane, with the transistor being associated with at least one reference electrode that is also immersed in the conductive medium; and the electrical signals induced by the pairing of the biological substances with the coupling substance on the sensitive membrane comprise variations in current or voltage.

10. The method of claim 9, wherein:
a potential ($V_{ds}$) between a drain and a source of the polarization voltage ($V_{pol}$) is assigned a constant value;
a drain current is kept constant, at an index value, with a potential between the reference and the source, $V_{rs}$, being adjusted; and
variations in $V_{rs}$ are measured in response to the pairings between the biological substances and the ligands on the sensitive membrane.

11. The method of claim 1, wherein the affinity sensor further comprises at least one other Sc/Is structure which does not include a sensitive membrane and in which the isolator Is and the semiconductor Sc form a field-effect transistor (FET) used as a reference (REFET).

12. A method of claim 1, further comprising:
interpreting the variations in electric signals to detect the biological substance.

* * * * *